United States Patent [19]

Warren, Jr.

[11] Patent Number: 5,389,302
[45] Date of Patent: Feb. 14, 1995

[54] CHEMILUMINESCENT DYE PENETRANT PROCESS AND COMPOSITION

[75] Inventor: Leslie F. Warren, Jr., Camarillo, Calif.

[73] Assignee: Rockwell International Corporation, Seal Beach, Calif.

[21] Appl. No.: 131,183

[22] Filed: Oct. 4, 1993

[51] Int. Cl.$^6$ .............................................. C09K 11/07
[52] U.S. Cl. .................... 252/408.1; 252/700; 436/3; 436/5; 436/904
[58] Field of Search ............... 252/700, 408.1; 436/3, 436/4, 5, 904

[56] References Cited

U.S. PATENT DOCUMENTS

| | | | |
|---|---|---|---|
| 3,716,494 | 2/1973 | Molina | 252/408.1 |
| 3,893,938 | 7/1975 | Rauhut | 252/700 |
| 3,973,466 | 8/1976 | Marcus et al. | 252/700 X |
| 3,992,319 | 11/1976 | Alburger | 252/408.1 |
| 4,641,518 | 2/1987 | Hutchings | 252/408.1 X |
| 4,717,511 | 1/1988 | Koroscil | 252/700 |
| 4,784,803 | 11/1988 | Bosotti | 252/700 |
| 4,858,465 | 8/1989 | Molina | 252/408.1 X |

*Primary Examiner*—Richard D. Lovering
*Assistant Examiner*—Valerie D. Fee
*Attorney, Agent, or Firm*—Charles T. Silberberg; Max Geldin

[57] ABSTRACT

A chemiluminescent dye penetrant composition is provided for detecting cracks and other defects in the surface of an object, which comprises a carrier, preferably in the form of a nonionic surfactant, a small amount of a fluorescent dye soluble in the surfactant and a minor amount of hydrogen peroxide. The dye penetrant is applied to the surface of the object and excess dye penetrant is removed therefrom. An oxalate ester or oxalate amide is then applied to the treated surface and reacts with the dye penetrant in the cracks and defects to luminesce, and produces self illuminated penetrant indications at the location of the cracks and defects. Oxalate esters such as bis(2,4,6 trichlorophenyl) oxalate are preferred. The oxalate ester or oxalate amide can be mixed with inert conventional developer materials such as talc or fumed silica.

13 Claims, No Drawings

CHEMILUMINESCENT DYE PENETRANT PROCESS AND COMPOSITION

BACKGROUND OF THE INVENTION

This invention relates to an improved dye penetrant process and composition, and is particularly directed to a chemiluminescent dye penetrant method and formulation for locating flaws and cracks on the surface of an object, particularly inside fuel cells and tanks or fueled aircraft in a manner so as to avoid an explosion hazard.

In known penetrant inspection methods for rapid location and evaluation of surface flaws such as cracks in test bodies or parts, a dye penetrant composition, preferably containing a fluorescent dye, and which will penetrate the openings of the surface of cracks or other voids in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks, to be drawn up out of the surface defects by capillary action. The part is then exposed to appropriate lighting conditions such as invisible fluorescigenous light, and the location of the surface cracks is revealed by the emission of visible fluorescent light by the penetrant dye which was retained in the cracks after the excess penetrant composition was removed from the surface of the part.

However, the detection of cracks and flaws or discontinuities in fuel tanks, particularly of aircraft, requires the use of expensive explosion proof equipment. Accordingly, there is a need to locate flaws and cracks inside fuel tanks or fueled aircraft in such a manner so as to avoid explosion hazards.

Chemiluminescent compositions are known in the prior art. Such compositions provide chemiluminescent light from a chemical reaction of an oxalate with a peroxide such as hydrogen peroxide in the presence of a fluorescent compound. Illustrative of such prior art are U.S. Pat. Nos. 3,893,938; 4,717,511; and 4,784,803.

OBJECTS OF THE INVENTION

It is an object of the present invention to provide an improved dye penetrant process and composition which does not require exposure to fluorescent light for illumination.

Another object is the provision of a dye penetrant process and composition which is chemiluminescent, or self illuminating, and does not require use of any external light source.

A still further object is to provide a dye penetrant process and formulation which is chemiluminescent, and utilizes similar application procedure as in prior art dye penetrant processes, but which avoids use of external light such as fluorescent light, while providing bright visible indications of cracks and flaws in an object surface which endure for an extended period.

SUMMARY OF THE INVENTION

According to the invention concept, a chemiluminescent penetrant formulation is applied to the surface of an object containing discontinuities or cracks and flaws therein, and after cleaning excess penetrant material from the surface of the object, applying a developer to cause the defects in the object surface to luminesce. The reaction is caused by the trapped material in the surface defects reacting with the applied developer.

More specifically, a method and composition for detecting cracks and other defects in the surface of an object are provided which comprises applying to the surface of the object a liquid dye penetrant comprising a dye carrier, particularly a nonionic surfactant, a small amount of a fluorescent dye soluble in the surfactant and a minor amount of hydrogen peroxide. Excess dye penetrant is removed from the surface of the object and a developer in the form of an oxalate ester or an oxalate amide is applied to the treated surface, at the location of the cracks and defects, causing the penetrant in the cracks and defects to luminesce and produce self illuminated penetrant indications at the location of the cracks and defects.

Various oxalate esters or amides can be employed for producing the chemiluminescent reaction, and such oxalate esters or amides can be employed per se as the developer, or such oxalate esters or amides can be mixed with inert developer material such as talc and fumed silica. Preferred oxalate esters are bis(chlorophenyl)oxalates.

DETAILED DESCRIPTION OF THE INVENTION AND PREFERRED EMBODIMENTS

As previously noted, the chemiluminescent dye penetrant composition of the invention comprises a carrier, a fluorescent dye soluble therein and hydrogen peroxide. Preferably the carrier for the dye is a nonionic surfactant.

The nonionic surfactant or carrier which is employed as the vehicle for the dye of the chemiluminescent dye penetrant composition according to the invention, includes any preferably water soluble nonionic surfactant of low viscosity which is compatible with the dye dissolved in the surfactant vehicle, and which are compatible with metals, particularly those employed in the aircraft industry, including aluminum, titanium and nickel alloys. Such nonionic surfactant must be capable of penetrating minute cracks and other defects on the surface of an object, to carry a film of dye composition into such cracks and other surface defects so as to reveal such cracks and defects.

A class of particularly preferred nonionic solvents or carriers which can be employed as vehicle for the fluorescent dye of the chemiluminescent dye penetrant compositions according to the invention are in the form of ethoxylates of a mixture of linear secondary aliphatic alcohols, with the hydroxyl groups randomly distributed, the linear aliphatic portion of said alcohols being a mixture of alkyl groups containing in the range from 11 to 15 carbon atoms, and containing an average of from 3 to 12 moles of ethylene oxide.

Illustrative examples of nonionic surfactants of the types noted above are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of nonionic surfactants are marketed, respectively, as:
Tergitol 15-S-3
Tergitol 15-S-5
Tergitol 15-S-7
Tergitol 15-S-9
Tergitol 15-S-12

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus, for example, Tergitol 15-S-5 is a mixture of linear aliphatic alcohols in the $C_{11}$ to $C_{15}$ range ethoxylated with an average of 5 moles of ethylene oxide.

Another class of nonionic solvents or carriers can be defined as straight chain primary aliphatic oxyalkylated alcohols, generally in the form of mixtures thereof, wherein the primary aliphatic alcohols can have preferably 10 to 18 carbon atoms, and the oxyalkyl groups are ethylene oxide and propylene oxide, preferably in the form of a mixture thereof.

Dye penetrant compositions containing nonionic surfactants as carrier or vehicle for the fluorescent dye, as defined above are disclosed, for example, in U.S. Pat. No. 4,186,304 to Molina. The disclosure of this patent is incorporated herein by reference.

Other nonionic surfactants can be employed as carrier or solvent for the fluorescent dye, such as nonyl phenyl polyethylene glycol ether. Ethoxylated nonylphenols can also be utilized as dye penetrant solvents.

If desired, optionally, extenders for lowering the viscosity of the dye penetrant can be incorporated therein, e.g. an isoparaffinic solvent consisting of a mixture of isoparaffins having carbon chains ranging from about 10 to about 17 carbon atoms in an amount ranging from about 0.5 to 15 parts, to 1 part of the sum of the surfactant and the dye, by volume, as also disclosed in the above Molina patent.

Another type of optional extender for the dye penetrant hereof is an N-alkyl-2-pyrrolidone, particularly N-methyl-2-pyrrolidone, employed in amounts noted above, as disclosed in U.S. Pat. No. 4,392,982 to Molina.

As previously noted, the dye penetrant solution employed according to the invention preferably contains a fluorescent dye. Various types of fluorescent dyes can be employed including for example the dye marketed as Fluorol 7GA and Morton Fluorescent Yellow G, as well as other fluorescent dyes such as those marketed as Calcofluor Yellow, Azosol Brilliant Yellow 6GF; Rhodanine B, Rhodanine 6 GDN, Calcofluor White RW, Blancophor White AW, Auramine and Eosine G, and water soluble fluorescent dyes such as Blancophor FFG. Other fluorescent dyes which can be employed include 1-chlorobis(phenylethynyl)anthracene, 9,10-diphenylanthracene, rubrene, Nile Red and fluorescein.

The amount of fluorescent dye which is incorporated into the nonionic, e.g. oxyalkylated alcohol, surfactant or carrier to produce the dye penetrant composition of the invention, can range from about 0.1 to 15, preferably about 0.5 to about 10, parts of the dye, or mixtures thereof, per 100 parts of such nonionic surfactant, by weight. In preparing the dye penetrant composition employed according to the invention the dye is simply added to the nonionic surfactant carrier, with or without extender.

Typical dye penetrant compositions to which the hydrogen peroxide can be added according to the invention are as follows:

TABLE 1

| COMPONENTS | Compositions (Parts by Weight) | | | |
|---|---|---|---|---|
| | A | B | C | D |
| Tergitol 15-S-5 | 75 | 75 | 50 | 100 |
| Tergitol 15-S-9 | 25 | 25 | — | — |
| Tergitol 15-S-3 | — | — | 50 | — |
| Calcofluor White RW | 5 | 2.5 | 5 | 5 |
| Fluorol 7 G A | 1.5 | 0.75 | 1.5 | 1.5 |

Hydrogen peroxide is introduced into the above dye penetrant composition containing carrier or nonionic surfactant and fluorescent dye. Such hydrogen peroxide can be applied as commercially available 30% hydrogen peroxide, 50% concentrated hydrogen peroxide, or 100% hydrogen peroxide. The hydrogen peroxide can be incorporated in the dye penetrant in an amount in the range of about 0.1 to about 10% by volume of 30% hydrogen peroxide. The carrier or nonionic surfactant for the dye is miscible with the hydrogen peroxide.

In the method for detecting cracks and other flaws on the surface of an object employing the chemiluminescent dye penetrant composition of the invention, such dye penetrant is applied to the part surface in any suitable manner, as by dipping or spraying. The low viscosity solvent penetrant quickly penetrates surface defects such as the cracks in the part surface, and immediately after application of the dye penetrant to the surface of the test part, the excess dye penetrant composition is readily removed from the object surface by water washing, e.g. by application of a water spray or by wiping with a water moistened cloth, followed by drying the part surface.

Following removal of excess dye penetrant from the part surface, an oxalate ester or an oxalate amide is applied to the part surface as so-called developer, preferably employing the oxalate ester. The oxalate ester or amide reacts with the hydrogen peroxide in the dye penetrant composition remaining in the cracks and flaws, in the presence of the fluorescent dye therein, to produce bright chemiluminescent or self illuminated indications of the cracks and flaws in the object surface over a prolonged period, e.g. about 1 to about 20 minutes. Preferably, the entire process can be carried out under reduced lighting or darkened conditions which provides greater sensitivity for detecting the self illuminated indications from the cracks and flaws, or following application of the developer the self illuminated indications from the cracks and defects can be viewed under reduced light or in darkness.

Various oxalate esters as powders can be employed for this purpose including bis(pentachlorophenyl) oxalate, bis(2,4,6-trichlorophenyl) oxalate, bis(phthalimido) oxalate, bis[1- (1H)-2-pyridonyl] glyoxal, bis(2-carbopentyloxy-3,5,6-trichlorophenyl) oxalate and bis(2,4-dinitrophenyl) oxalate. The bis(chlorophenyl) oxalates such as bis (pentachlorophenyl) oxalate (BTCPO) and bis(2,4,6 trichlorophenyl) oxalate (BTCPO), are particularly effective. Oxalate amides which can be used are, for example, quaternary salts of N,N'-bis(morpholinoalkyl)-N,N'-bis(trifluoromethylsulfonyl) oxamides, and pyridyl analogues.

After application of the oxalate ester to the part surface, excess oxalate can be removed, as by means of an air blast.

If desired, the oxalate ester or oxalate amide can be mixed with inert conventional developer materials such as talc, fumed silica, alumina and titanium dioxide, and mixtures thereof. Developer powders containing 25–65% talc and 35–75% fumed silica, by weight, are disclosed in U.S. Pat. No. 4,069,419 to Molina. Thus, such a developer powder can contain a minor portion of the oxalate ester or oxalate amide and a major portion of a mixture of talc and fumed silica, e.g. an amount of about 1 to about 10% of oxalate ester based on the weight of the talc-fumed silica mixture, which mixture can be a 1:1 mixture of talc and fumed silica, by weight. If desired, such developer composition can be prepared by dissolving the oxalate ester or oxalate amide in a solvent such as benzene, adding the silica/talc mixture and allowing the solvent to evaporate at room temperature. Alternatively, the oxalate ester or amide, and inert developer powder such as talc and fumed silica can be mixed dry as powders. Such powders can be applied to the part surface in the usual fashion as a dry developer powder or as a wet non-aqueous developer composition, e.g. as by spraying from a dispersion in isopropanol.

The following are examples of practice of the invention:

EXAMPLE 1

1 part by volume of 30% hydrogen peroxide is added to 20–30 parts by volume of dye penetrant composition C of Table 1 above.

The peroxide-treated penetrant composition C was applied to the surface of an object to be tested in the conventional manner, i.e. by wiping on with a cloth, with the excess penetrant being removed by rinsing with water and wiping with a cloth, and drying.

The oxalate ester BTCPO powder was then applied to the treated surface employing a brush and the oxalate ester particles reacted with exposed penetrant in the cracks and flaws to produce visible self illuminated light (yellow green) indications thereof, which lasted when viewed under darkened conditions, for 10 minutes.

EXAMPLE 2

The procedure of Example 1 was repeated but employing the oxalate ester BPCPO.

Equally good results were obtained as in Example 1.

EXAMPLE 3

The procedure of Example 1 was substantially followed except that the developer powder employed was a mixture of 1% of the oxalate ester BTCPO in a 1:1 mixture of talc and fumed silica, by weight. This was prepared by dissolving 0.05 g of BTCPO in 100 ml of benzene, adding 5 g of the silica/talc mixture, stirring and allowing to evaporate at room temperature. The resulting powder was dispersed in isopropanol, and the dispersion was sprayed on the part surface and excess developer was removed from the part surface.

Bright self illuminated indications of the cracks and flaws were obtained as in Example 1.

EXAMPLE 4

The procedure of Example 3 was essentially followed except that the developer powder was formed of 10% of the oxalate ester BTCPO in a 1:1 mixture of talc and fumed silica, by weight, by dissolving 0.5 g of BTCPO in 100 ml of benzene, adding 5 g of the silica/talc mixture, and evaporating.

Results similar to Example 3 were obtained.

EXAMPLE 5

The procedure of Example 1 was substantially followed except employing as the dye penetrant composition of nonionic surfactant and fluorescent dye, composition A of Table 1.

Results similar to Example 1 were obtained.

From the foregoing, it is seen that the invention provides a chemiluminescent improved dye penetrant composition formed of a dye carrier, particularly a nonionic surfactant, a fluorescent dye and hydrogen peroxide which upon application to a part surface containing flaws and cracks can be developed by the application of an oxalate ester or oxalate amide to provide a reaction which results in chemiluminescence or self illumination of the dye penetrant in the cracks and flaws, providing self illuminated penetrant indications in the areas of such surface discontinuities.

Since various changes and modifications can be made in the invention without departing from the spirit of the invention, the invention is not to be taken as limited except by the scope of the appended claims.

What is claimed is:

1. A method for detecting cracks and other defects in the surface of an object which comprises
   applying to said surface a liquid dye penetrant comprising a dye carrier in the form of a nonionic surfactant, a fluorescent dye soluble in said carrier in an amount of about 0.1 to about 15 parts of said dye per 100 parts of said surfactant, by weight, and hydrogen peroxide in an amount equivalent to about 0.1 to about 10% by volume of 30% hydrogen peroxide,
   removing excess dye penetrant from the surface of said object, while retaining dye penetrant in said cracks and defects,
   applying an oxalate selected from the group consisting of an oxalate ester and an oxalate amide to the treated surface, causing said penetrant in said cracks and defects to luminesce, and thereby producing self illuminated penetrant indications at the location of said cracks and defects.

2. The method of claim 1, employing an oxalate ester.

3. The method of claim 2, said oxalate ester being a bis(chlorophenyl) oxalate.

4. The method of claim 3, said oxalate ester selected from the group consisting of bis(pentachlorophenyl)oxalate and bis(2,4,6-trichlorophenyl) oxalate.

5. The method of claim 1, said dye carrier comprising a liquid nonionic surfactant in the form of ethoxylates of a mixture of linear secondary aliphatic alcohols, with the hydroxyl groups randomly distributed, the linear aliphatic portion of said alcohols being a mixture of alkyl groups containing in the range from 11 to 15 carbon atoms, and containing an average of from 3 to 12 moles of ethylene oxide.

6. The method of claim 1, said oxalate ester being in the form of a developer powder containing a minor portion of said oxalate ester and a member selected from the group consisting of talc, fumed silica, alumina, titanium dioxide, and mixtures thereof.

7. The method of claim 1, said oxalate ester being in the form of a developer powder containing a minor portion of said oxalate ester and a major portion of a mixture of talc and fumed silica.

8. The method of claim 7, said oxalate ester being present in an amount of about 1 to about 10% based on the weight of the talc/fumed silica mixture, said mixture being a 1:1 mixture of talc and fumed silica, by weight.

9. A method for detecting cracks and other defects in the surface of an object which comprises applying to said surface a liquid dye penetrant comprising a major amount of a liquid nonionic surfactant in the form of ethoxylates of a mixture of linear secondary aliphatic alcohols, with the hydroxyl groups randomly distributed, the linear aliphatic portion of said alcohols being a mixture of alkyl groups containing in the range from 11 to 15 carbon atoms, and containing an average of from 3 to 12 moles of ethylene oxide, a fluorescent dye in an amount of about 0.1 to about 15 parts of said dye per 100 parts of said surfactant, by weight, and hydrogen peroxide in an amount equivalent to about 0.1 to about 10% by volume of 30% hydrogen peroxide, removing excess dye penetrant from the surface of said object, while retaining dye penetrant in said cracks and defects, applying a bis(chlorophenyl) oxalate to the treated surface, causing said penetrant in said cracks and defects to luminesce, thereby producing self illuminated penetrant indications at the location of said cracks and defects, and observing said self illuminated penetrant indications under reduced lighting conditions.

10. The method of claim 9, wherein said oxalate ester selected from the group consisting of bis(pentachlorophenyl)oxalate and bis(2,4,6trichlorophenyl) oxalate.

11. The method of claim 9, said oxalate ester being in the form of a developer powder containing a minor portion of said oxalate ester and a major portion of a mixture of talc and fumed silica.

12. A liquid dye penetrant composition for use in non-destructive testing for detecting cracks and other defects in the surface of an object comprising a liquid nonionic surfactant, a fluorescent dye in said surfactant, in an amount of about 0.1 to about 15 parts of said dye per 100 parts of said surfactant, by weight, said dye being soluble in said surfactant, and hydrogen peroxide in an amount equivalent to about 0.1 to about 1.0% by volume of 30% hydrogen peroxide.

13. The dye penetrant composition of claim 12, said surfactant being in the form of ethoxylates of a mixture of linear secondary aliphatic alcohols, with the hydroxyl groups randomly distributed, the linear aliphatic portion of said alcohols being a mixture of alkyl groups containing in the range from 11 to 15 carbon atoms, and containing an average of from 3 to 12 moles of ethylene oxide.

* * * * *